US009259287B2

(12) United States Patent
Mansi et al.

(10) Patent No.: US 9,259,287 B2
(45) Date of Patent: Feb. 16, 2016

(54) PATIENT SPECIFIC PLANNING AND SIMULATION OF ABLATIVE PROCEDURES

(71) Applicants: Tommaso Mansi, Westfield, NJ (US); Puneet Sharma, Monmouth Junction, NJ (US); Viorel Mihalef, Keasbey, NJ (US); Ali Kamen, Skillman, NJ (US); Saikiran Rapaka, Ewing, NJ (US); Dorin Comaniciu, Princeton Junction, NJ (US)

(72) Inventors: Tommaso Mansi, Westfield, NJ (US); Puneet Sharma, Monmouth Junction, NJ (US); Viorel Mihalef, Keasbey, NJ (US); Ali Kamen, Skillman, NJ (US); Saikiran Rapaka, Ewing, NJ (US); Dorin Comaniciu, Princeton Junction, NJ (US)

(73) Assignee: SIEMENS AKTIENGESELLSCHAFT, München (DE)

( * ) Notice: Subject to any disclaimer, the term of this patent is extended or adjusted under 35 U.S.C. 154(b) by 73 days.

(21) Appl. No.: 13/854,991

(22) Filed: Apr. 2, 2013

(65) Prior Publication Data
US 2014/0296842 A1  Oct. 2, 2014

(51) Int. Cl.
*A61B 18/12* (2006.01)
*A61B 19/00* (2006.01)
*A61B 18/00* (2006.01)

(52) U.S. Cl.
CPC ............. *A61B 19/50* (2013.01); *A61B 18/1233* (2013.01); *A61B 2018/00577* (2013.01); *A61B 2019/504* (2013.01); *A61B 2019/505* (2013.01)

(58) Field of Classification Search
CPC .... A61B 18/18; A61B 18/1206; A61B 19/50; A61B 2019/504; A61B 2019/505; A61B 18/1233
USPC .......................... 606/32–35, 41; 607/101–105
See application file for complete search history.

(56) References Cited

U.S. PATENT DOCUMENTS

| 7,871,406 | B2 * | 1/2011 | Nields et al. | 606/27 |
|---|---|---|---|---|
| 2011/0015628 | A1 * | 1/2011 | Dalal et al. | 606/34 |
| 2011/0144967 | A1 * | 6/2011 | Adirovich | 703/11 |
| 2011/0224664 | A1 * | 9/2011 | Bar-Tal et al. | 606/33 |
| 2011/0275936 | A1 * | 11/2011 | Cho et al. | 600/438 |
| 2012/0283564 | A1 * | 11/2012 | Ebbini et al. | 600/439 |
| 2013/0035921 | A1 * | 2/2013 | Rodriguez-Ponce et al. | 703/11 |
| 2013/0070201 | A1 * | 3/2013 | Shahidi et al. | 351/206 |
| 2013/0184700 | A1 * | 7/2013 | Dalai et al. | 606/33 |
| 2014/0136174 | A1 * | 5/2014 | Audigier et al. | 703/11 |

* cited by examiner

*Primary Examiner* — Michael Peffley
*Assistant Examiner* — Thomas Giuliani (57) ABSTRACT

Patient specific temperature distribution in organs, due to an ablative device, is simulated. The effects of ablation are modeled. The modeling is patient specific. The vessel structure for a given patient, segmented from medical images, is accounted for as a heat sink in the model of biological heat transfer. A temperature map is generated to show the effects of ablation in a pre-operative analysis. Temperature maps resulting from different ablation currents and ablation device positions may be used to determine a more optimal location of the ablative device for a given patient. Other models may be included, such as accounting for the tissue damage during the ablation.

19 Claims, 2 Drawing Sheets

PATIENT SPECIFIC PLANNING AND SIMULATION OF ABLATIVE PROCEDURES

BACKGROUND

The present embodiments relate to ablation planning. In particular, computation of temperature maps is provided.

Ablation is one option for cancer treatment. In spite of recent advances in cancer therapy, treatment of primary and metastatic tumors of the abdomen remains a significant challenge. Hepatocellular carcinoma (HCC) for example is one the most common malignancies encountered throughout the world (e.g., >1 million cases per year). In the U.S. alone, 1 in 153 individuals will develop HCC with reported 5-year survival rates of less than 15%.

For both primary liver cancer and hepatic metastases, liver resection (partial hepatectomy) is the current preferred option in patients having confined disease. In selected cases of early HCC, total hepatectomy with liver transplantation may also be considered. Unfortunately, less than 25% of patients with primary or secondary liver cancer are candidates for resection or transplantation, primarily due to tumor type, location, or underlying liver disease. Consequently, increasing interest has been focused on ablative approaches for the treatment of unresectable liver tumors. Rather than extirpation, this technique uses complete local in situ tumor destruction. A variety of methods have been employed to locally ablate tissue. Radiofrequency ablation (RFA) is the most commonly used, but other techniques are also used, including ethanol injection, cryo-therapy, irreversible electroporation, and microwave ablation.

The RFA procedure is performed by placing a probe within the target area, the tumor, in the liver parenchyma. Electrodes at the tip of the probe create heat, which is conducted into the surrounding tissue, causing coagulative necrosis at temperatures between 50° C. and 100° C. In addition to increasing the number of patients eligible for curative therapy of liver cancer in unresectable patients, local tissue ablation has a significant advantage as ablation may be performed using a minimally invasive approach, including percutaneously and laparoscopically.

To place the probe at the target location, the physician relies on intra-operative imaging techniques, such as ultrasound. However, the success of the procedure depends on the optimal placement of the probe and heat delivery. Different placements may have different results. The success of ablation is further challenged by the hepatic blood vessels that dissipate heat, thus potentially reducing RFA efficiency.

BRIEF SUMMARY

By way of introduction, the preferred embodiments described below include methods, computer readable media and systems for patient specific computation of temperature distribution under ablation therapy. The effects of ablation are modeled. Using data from a specific patient, the modeling may be patient specific. The vessel structure for a given patient is accounted for as a heat sink in the model of biological heat transfer. Based on the model, a temperature map is generated to show the effects of ablation in a pre-operative analysis. Temperature maps resulting from different ablation currents and/or ablation positions may be used to determine a more optimal location for ablation for a given patient. Other models may be included, such as accounting for the change in tissue damage during the ablation.

In a first aspect, a method is provided for patient specific computation of temperature distribution under ablation therapy. An imaging system acquires imaging data representing tissue of a patient and blood vessels. A heat sink in the tissue is modeled with computational fluid dynamics. The modeling of the heat sink is a function of locations of the vessels in the tissue region of the patient from the imaging data. Biological heat transfer in the tissue is modeled as a function of the heat sink model. A map of temperature from an ablation device is calculated as a function of the biological heat transfer. An image of the computed map of temperature is displayed.

In a second aspect, a non-transitory computer readable storage medium has stored therein data representing instructions executable by a programmed processor for patient specific computation of a temperature map under ablation therapy. The storage medium includes instructions for simulating heat generation by an ablation device, simulating diffusion over time of the heat in tissue, the diffusion responsive to heat sink operation of blood vessels in the tissue of a patient, the blood vessels being specific to the patient, and the diffusion responsive to time-varying tissue response to the heat of the tissue, and indicating the diffusion.

In a third aspect, a system is provided for patient specific computation of a temperature map under ablation therapy. An imaging system is configured to scan a patient and output imaging data representing a tissue and vessels of the patient. A processor is configured to predict ablation results in the tissue region of the patient from a model of the ablation device, a position of the modeled ablation device, a model of heat sink effect of the vessels, and a model of diffusion of heat transfer due to the model of the ablation device, the position, and heat sink operation.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Patient specific planning and simulation of ablative procedures is provided. A planning and simulation engine may be utilized to optimize the placement of radiofrequency ablation (RFA) or other ablation probes and the delivered heat or cold power for maximally effective thermal dose leading to complete tumor death.

Computer models of heat diffusion in biological tissues, tissue thermal properties and reaction to the heat, and the effect of nearby vessels, which act as heat sinks, are included in the simulation. The simulation uses a patient specific model of the vascular system. The patient specific model takes into account accurate topology and diameter of the vessel segments and the geometry of the organ, takes into account the blood flow and dynamics of the flow within the context of heat diffusion, and provides an efficient numerical scheme to solve for the system of equations.

Figure 1:
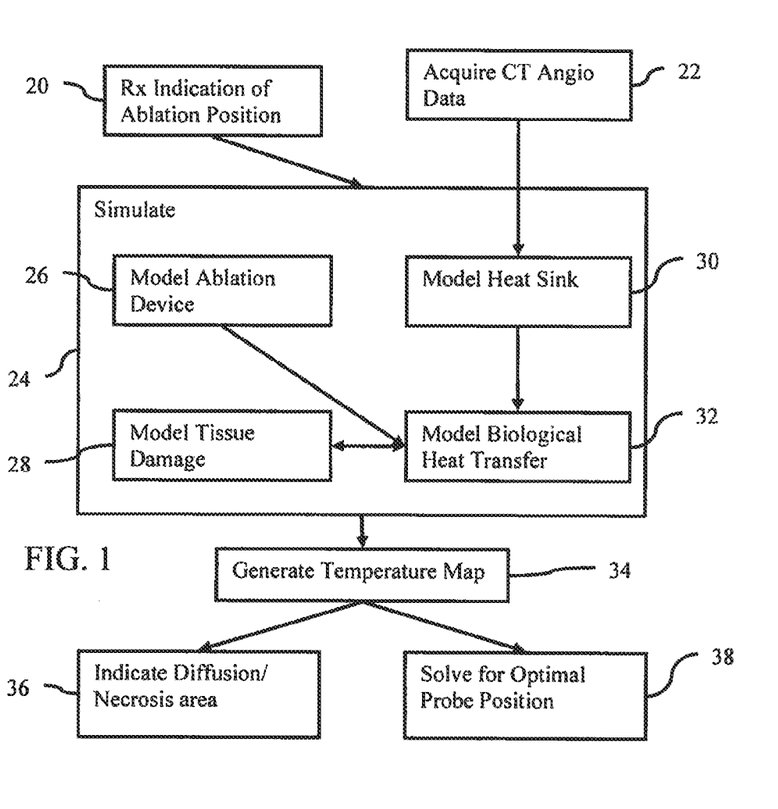
FIG. 1 is a flow chart diagram of one embodiment of a method for patient specific computation of a temperature map under ablation therapy.

FIG. 1 shows a method for patient specific computation of temperature maps. The method is implemented by a medical diagnostic imaging system, a review station, a workstation, a computer, a PACS station, a server, combinations thereof, or other device for processing medical planning data. For example, the system or computer readable media shown in FIG. 4 implements the method, but other systems may be used.

The method computes temperature maps for planning ablation. For example, ablation of one or more liver tumors is planned. Planning for liver cancer or other treatment of other organs (e.g., lung, kidneys, breast and bones) may be provided. The same method is performed as the governing model and corresponding equations are applicable to different kinds of biological tissue. The tissue properties in one or more models may vary based on the tissue of interest. Similarly, model-based planning of radiofrequency ablation of cardiac arrhythmia rather than cancer treatment may be provided. The extent of the ablated myocardial tissue may be predicted.

The method is implemented in the order shown in FIG. 1 or a different order. For example, acts 20 and 22 are performed in any order or simultaneously. As another example, the various modeling acts 26-32 in simulation 34 are performed in any order or as needed to implement the heat diffusion estimation of act 32. Additional, different, or fewer acts may be performed. For example, act 26 and/or act 28 are not performed. Acts 36 and/or act 38 may or may not be performed.

The acts may be performed automatically by a processor. The user causes the patient to be scanned or obtains scan data for the patient from a previous scan. The user may control the position, orientation, power, and/or other aspect of the simulated ablation device. The user may activate the process. Once activated, the simulation of act 24 is performed without further user input other than position and/or power. User input of locations of the anatomy or temperature may be avoided. Some user input may be provided, such as for changing modeling parameter values, correcting locations, assisting in segmentation of tissue or vessels, and/or to confirm accuracy.

In act 20, a user indication of a placement position of the ablation device is received. The ablation is to occur near or in a lesion (e.g., tumor) or other region of tissue. Given anatomy, type of ablation, type of ablation device, or other limitations, the placement in the tissue may be limited. The user indicates a possible placement by selecting a location or locations in one or more images. For example, a location in a multi-planar reconstruction of the patient is indicated.

Multiple placements may be provided. For example, the user indicates a sequence of placements for simulating sequential ablation operations or applications. The sequence is simulated by re-running the simulation act 24 with an updated probe position, power setup, and duration using the results from the previous run. Using the modeling of tissue damage in act 28, the changed tissue properties for various locations may be considered during the subsequent runs. Sequential placement may be used for larger tumors, where the single probe placement does not provide sufficient coverage of the thermal dose to the tumor.

As another example, the user indicates multiple placements for simulating ablation using multiple devices at a same time. The aggregated thermal dose is computed based on a single simulation run.

In an alternative embodiment, the user does not indicate placement. Instead, the position is selected based on image data, such as identifying a center of the tumor. Various possible placements may be automatically identified and tested with separate simulations. Other automatic approaches may be used.

The user also inputs the type of ablation, duration, a desired dose, an indication of the spatial extent of the tumor, an indication of a location in the tumor, an amount of power for ablation, a type of ablation device, a sequence of power, and/or other characteristic of the ablation or tissue. Various inputs may be automated. Instead of user input, a process provides the information.

In act 22, data representing an organ or other tissue and vessels in the tissue or organ of a patient is acquired. A preoperative volume is acquired. The data represents locations distributed in three dimensions. The volume is a frame or set of data representing part or the entire tissue region of interest, such as the liver or part of the liver. The data may represent other portions of the patient, such as part of an adjacent organ, bone, fluid, or other structure in the patient.

The preoperative data is acquired by scanning the patient prior to an ablation procedure. For example, the patient is scanned in one room to acquire the preoperative data, and then the ablation device is inserted in another room or the same room for the intervention procedure. The preoperative data may be acquired the same day or different day than the occurrence of the ablation procedure. In alternative embodiments, the data is acquired after one or more ablation procedures, but prior to another.

The preoperative data is acquired using one or more modes of imaging. For example, ultrasound, magnetic resonance, computed tomography (CT), positron emission tomography, single photon emission computed tomography, or combinations thereof are used. In one embodiment, a computed tomography, fluoroscopy, x-ray, or CT angiography system is used. The patient may ingest or be injected with a contrast agent that is generally opaque to x-rays. The contrast agent collects or is in the circulatory system, so vessels contrast with tissue. Any scanning sequence or approach may be used, such as CT angiography modes or rotational angiography.

In an alternative embodiment, the preoperative volume is acquired by loading from memory. Data from a previously performed scan of the patient is stored in a memory, such as a picture archiving and communications system (PACS) database. The preoperative data is selected from the database. The preoperative volume may be acquired by transfer, such as over a network or on a portable memory device.

To model the heat sink provided by blood flow, vessels are segmented from the data. For example, angiographic information representing locations in three-dimensions is thresholded. Due to the contrast agent in the vessels, the vessels have a different intensity than soft tissue or bone. Thresholding identifies the locations of the vessels. In another example, a graph theory approach is used, such as a random walker. The user or processor indicates seed locations in and out of the vessel structure. Borders of the vessels with other structure are located. Other approaches include a machine-trained classifier for segmentation. Any automatic, semi-automatic or user tracing segmentation may be used. The centerline, border, and/or other location of the vessels are found.

By identifying locations of the vessels in an organ of interest (e.g., liver), the simulation of ablation may be personalized. Patient-specific planning may be performed as different vessel structures, distributions, sizes, blood density, blood heat capacity, flow rates, and/or variance may result in different heat diffusion in the tissue. In one embodiment, the segmentation provides the vessel structure, distribution, and size specific to a patient, while blood density, blood heat capacity, flow rates, and variance are treated as nominal values for the tissue or organ of interest.

The organ, other tissue, and/or the tumor of interest may be segmented from the same or different set of data. The same or different type of segmentation is used. Where different sets of data from the same or different imaging modalities are used for the different segmentations, the sets are spatially aligned. Sensors, data correlation, fiducial alignment, or acquisition in a same frame of reference provide the relative positions of the segmented information.

In one embodiment, the liver geometry and the venous system are segmented from a preoperative computed tomography (CT) data or image. An algorithm segments the liver and venous system. For example, an anatomical model of the patient's liver, which includes liver parenchyma, tumors, hepatic vein, and portal vein, is estimated. The 3D surface of the liver may be segmented automatically from medical images (ultrasound, magnetic resonance, or computed tomography (CT), or rotational angiography). In one embodiment, the model is semi-automatically estimated from the CT data using a graph theory approach, such as a random walker. For each structure, the user defines seeds inside and outside the area of interest. Then, the random-walker algorithm automatically estimates the boundary of the structure. The process may be refined by the user, interactively.

The resulting segmentations are available for simulation of heat diffusion. In one embodiment, the segmented structures are merged or combined into a data set. The data set represents the different structures. For example, a multi-label mask image or data set is used to generate a tetrahedral multi-domain mesh. The volumetric tetrahedral mesh is generated from the detected surface of the organ. The mesh has enough resolution to integrate the blood vessels obtained from the 3D image. Other mesh topology may be used. Alternatively, the continuous surfaces or the segmented structures are used.

In act 24, the ablation procedure is simulated. Any number of models for simulation may be used. FIG. 1 shows four models. In other embodiments, some modules are not used. In yet other embodiments, one or more models are combined. Additional models may be included. Different models may be used. Each model represents an equation, algorithm, machine-learnt matrix, or other process.

In act 26, the ablation device is modeled. Any model providing an output of the heat, power, intensity or other measure of application may be used. The measure is provided as a function of time where the measure varies over time, such as associated with cycles or variation of power or ablation, warm-up time, and/or cool-down time. In other embodiments, the measure is treated as constant.

In one embodiment for radio frequency ablation, the ablation device is modeled as a function of resistance, current, and time. The heat generation by the ablation device is simulated using a resistance of the particular ablation device, the current indicated by the user or processor, and time of application. The input is the electrical power delivered to the probe. How the electrical current at the probe is transformed to the heat source at the surface of the probe is modeled to have a virtual radio frequency ablation engine that closely reproduces the actual protocol. For example, Joule's first law, $Q=I^2 R t$, where Q is the heat generated by the current I, R is the resistance of the probe, and t is time, is used. The probe location may be fixed in space but the current may vary over time.

In other embodiments, cryotherapy or microwave ablation is modeled. In cryotherapy, the cells are destroyed by very low temperature. Cryotherapy is similar to radiofrequency ablation as temperature is used and the temperature diffusion is similar or the same for heat and cold. Microwave ablation is different regarding the generation of heat. Nonetheless, the proposed method may be easily adapted as cellular death, optimization of needle placement, and heat convection are similar. The heat source may be modeled as a Dirichlet boundary condition in a specific tissue region. The model for creation of the heat and the locations of the creation over time is directed to microwave application.

In act 28, tissue damage is modeled. As heat (or cold) is applied, tissue is damaged. Cells die. Tissue necrosis occurs. The result may alter temperature diffusion. Dead or treated tissue may not conduct heat in the same way or rate as in healthy tissue. One or more aspects of heat transfer may be different due to the change in the tissue.

Any model of tissue damage may be used. In one embodiment, the tissue damage is modeled using a survival fraction index and an Arrhenius-like equation. The tissue damage model is experimentally determined, extracted from studies, or created from theory. The survival fraction index indicates the amount of live versus dead cells in a region as a function of temperature. The survival fraction index is calculated from the current temperature using an Arrhenius-like model. More precisely, the survival fraction index is the ratio of viable cells to the total number of cells in a region of interest. When the survival fraction index is $\ll 1$, cells in this spatial region are dead. The Arrhenius equation models the relationship of the survival fraction with respect to temperature.

In another embodiment, the tissue damage is modeled as three or other number of states. The model computes the variation of concentration of live cells (A), vulnerable cells (C), and dead cells (D) over time according to the state equation: $A \leftarrow_{Kb} \rightarrow V \rightarrow_{Kf} D$ where Kf and Kb are the rates of cell damage and recovery, respectively. In particular, Kf depends on the temperature through the equation: $Kf = kf\, e^{T/Tk}(1-A)$ with kf being a scaling constant and Tk a parameter that sets the rate of the exponential increase with temperature. This equation results in three simultaneous ordinary differential equations, solved at each node of the computational domain, yielding spatially-varying cell state field. Any temporal integration scheme may be used (e.g. first order Euler explicit or first order Euler implicit). The initial conditions are chosen as A=0.99, V=0.01 and D=0.00, but other values may be used. Additionally, dead or damaged cells do not have the same heat capacity ct as live cells. This phenomenon can affect heat transfer and ablation extent. Each time step of the computation is updated with the state of the cells, given the cells current temperature. The corresponding heat capacity ct is used if healthy or vulnerable, dead cells have a fixed heat capacity of $c_t^*$. Other cell death models may be used.

In one embodiment, various values are used. Example values of model parameters for the tissue damage are:
$k_f$—forward rate constant=$3.33 \times 10^{-3}$ s$^{-1}$
$k_b$—backward rate constant=$7.77 \times 10^{-3}$ s$^{-1}$
$T_k$—parameter of cell state model=40.5° C.

In act 30, the simulation of act 24 is personalized by modeling the heat sink provided by blood flow in the tissue region. The heat sink modeling depends on the blood flow. Locations of the vessels in the tissue region, the size of the vessels, and/or other vessel characteristics are used to model the heat sink characteristics in the region of interest. The characteristics may be extracted from the segmented vessel information.

The flow rate of the blood in the vessels is computed. The flow rate may be an average over a heart cycle or may include variation in flow rate through one or more heart cycles. The model outputs the flow rate, volume flow, or other flow related characteristic based on input information, such as the diameter of the vessels. The biological heat transfer model may include the locations and the flow rate of the vessels for modeling heat diffusion.

The flow rate is computed for vessels along three-dimensional vessel paths. Only larger vessels (e.g., feeder vessels), such as vessels over a threshold diameter within a specific distance from the treatment location, are modeled. Heat loss due to smaller vessels (e.g., tree or branching vessels) may be ignored. Alternatively, the heat loss due to smaller vessels is also modeled.

The flow rate for larger vessels is computed with computational fluid dynamics. The flow rates in the feeding vessels, whose patient-specific geometry is extracted in the segmenting of act 22, are calculated. With sufficient resolution, the flow rates in smaller vessels may be computed. The geometric model of the flow includes the main vessels further bifurcating into an underlying tree structure for small vessels. To efficiently compute the flow rates in the vessels of the vessel tree, a coupled 3d-1d computational fluid dynamics approach is used. Each three-dimensional small vessel is treated as a one-dimensional structure. The radius and length of the tree vessels are used to determine the flow rates of the tree vessels. Alternatively, the same technique is used to determine the flow rate in all of the vessels above a threshold size and the smaller vessels are ignored.

Flow at a micro scale may be ignored. Alternatively, the perfusion flow rate is computed using other flow rates, such as the feed flow rate for the larger vessels and the tree flow rates for smaller vessels. The anisotropic perfusion rates at microscale are determined.

In one embodiment, the liver is treated as a porous media, so solving Darcy's law provides a velocity field throughout the organ used in the advection part of the heat transfer model. The blood velocity v inside the parenchyma is calculated according to Darcy's law: $v=-k/(\mu e^{2/3})$del·p, where p is the pressure within the parenchyma and $\mu$ is the dynamic viscosity of the blood flow. This amounts to solving the Laplace equation del·$((-k/(\mu e^{2/3})$del·p$)=0$. At the border of the liver, Neumann boundary conditions are employed as no or little flow leaks outside the liver, whereas at the tip of portal and hepatic veins, Dirichlet boundary conditions are applied. Since the pressures cannot be estimated in-vivo, a computational fluid dynamics (CFD) model of the hepatic venous circulation system is used to estimate the pressures. Let $\phi_{vcin}$ be the vena cava inflow, $\phi_p$ the portal vein inflow, and $\phi_{vc}$ be the vena cava outflow, which in virtue of conservation of mass is equal to $\phi_{vcin}+\phi_p$. The hepatic artery may be ignored or included as well. A small pressure is assumed to exist at the outlet of the vena cava (e.g., $p_0=1$ mmHg).

The blood flow and pressure distribution are computed within the vena cava using three-dimensional computational fluid dynamics (e.g., using unsteady incompressible Navier-Stokes equations with viscous terms). The blood is modeled as a Newtonian fluid with pre-specified density (e.g., density=1:05 g/cm$^3$) and viscosity (e.g., viscosity=0:004 Pa s). The parameters may be different from one patient to another. A plug profile velocity field is applied at the inlets, computed from the outflow $\phi_p$ and the cross-sectional area of each inlet. From the computational fluid dynamics computation, the downstream pressures $p_i^-$ for each inlet of the vena cava is provided. The upstream pressure $p^+$ is assumed constant such that the computed perfused flow through the vena cava inlets matches the three-dimensional computational fluid dynamics inlet flow profiles. Once $p^+$ is estimated, the blood flow inside the portal vein is computed using the three-dimensional computational fluid dynamics solver.

The effect of heat on the viscosity of the flow may be neglected. As a result, flow related computation is performed before the simulation of heat diffusion. In alternative embodiments, the effect is modeled and the modeling of acts 30 and 32 are coupled over time.

In act 32, the biological heat transfer in the tissue region is modeled. The diffusion of heat over time in the tissue is simulated. The diffusion or progression of temperature change over time and space is calculated. A temperature distribution field is solved as a function of time using a partial differential equation or other equation. The numerical solution of the bio-heat transfer equations yields an underlying temperature distribution field that varies in space and time.

In one embodiment, a modified Pennes bio-heat transfer equation is used. The spatio-temporal temperature variation is balanced by a transient heat diffusion term, a heat source term, and at least one convective term. The modified Pennes bio-heat transfer equation may be represented as:

$$\rho c \frac{\partial T}{\partial t} = \nabla \cdot (\alpha_{t,x} \nabla T) - \beta_{t,x}^{perf}(T - T_b) - \beta_{t,x}^{flow}(T - T_b) + p(x, t)$$

In this model, the temporal temperature variation $$\left(\rho c \frac{\partial T(x, t)}{\partial t}\right)$$

is balanced by the heat diffusion term ($\nabla \cdot (\alpha_{t,x} \nabla T)$), together with two convective terms, $\beta^{perf}$ and $\beta^{flow}$, to account for the heat transfer to the blood, and a source term p(x, t) to account for the heat source from the ablative device. The biological heat transfer model includes terms for the density, $\rho$, specific thermal capacity constant, c, and anisotropic thermal conductivity matrix, $\alpha_{t,x}$. Additional, different, or fewer terms may be used, such as only one convective term. Other models may be used.

In general, computing heat diffusion in biological tissues amounts to solving the coupled bio-heat equations derived from the theory of porous media, where each elementary volume is assumed to comprise a tissue fraction and a blood fraction. In the Pennes model, the blood temperature is assumed constant, which holds close to large vessels, where blood velocity is high. An alternative, more simplified expression of the Pennes model may thus be:

$(1-\epsilon)p_t c_t(\delta T_t/\delta t)=(1-\epsilon)Q+(1-\epsilon)del \cdot (d_t del \cdot T_t)+H(T_{b0}-T_t)$.

In this equation, the parameter H relates to both $\beta^{Perf}$ and $\beta^{flow}$ of the previous equation and Q relates to the source term p(x,t).

The above-mentioned Pennes bio-heat transfer equation may consider the big vessels, feeder vessels, tree vessels, micro vessels, or combinations thereof. In an alternative embodiment, the feeder vessels from the segmentation of act 22 are considered using the Pennes model and the tree or small arteries are considered using the contribution of a Wulff-Klinger model. An equilibrium between tissue and blood temperatures is assumed (Tt=Tb) in the Wulff-Klinger model, so is well-suited for modeling velocity in small vessels, where blood velocity is low. The Wulff-Klinger model is represented as:

$$(1-\epsilon)p_t c_t(\delta T_t/\delta t)=(1-\epsilon)Q+(1-\epsilon)del\cdot(d_t del\cdot T_t)-\epsilon p_b c_b v\cdot del\cdot T_t.$$

In both equations, T is the temperature, Q is the source term and v is the blood velocity. Subscripts t and b refer to tissue and blood phases respectively. $T_{b0}$ is the mean temperature, which is assumed to be constant, of the blood in the portal and hepatic veins. Example values of model parameters are provided in Table 1.

Table 1.
$p_b$, $p_t$—blood and tissue densities=$1.06 \times 10^3$ kg m$^{-3}$
$c_b$—blood heat capacity=$4.18 \times 10^3$ J(kg K)$^{-1}$
$c_t$—tissue heat capacity=$3.6 \times 10^3$ J(kg K)$^{-1}$
$c_{t\_}$—tissue heat capacity in dead cells=$0.67 \times 10^3$ J(kg K)$^{-1}$
$d_b$, $d_t$—blood and tissue heat conductivities=$0.512 \times (1+0:00161 \times (T-310))$ W(m K)$^{-1}$
H—convective transfer coefficient=$24.4 \times 10^4$ W (m$^3$ K)$^{-1}$
$\epsilon$—blood volume fraction=0.1
κ—permeability=$2.0 \times 10^{-2}$ m$^2$
μ—dynamic viscosity=$4.6 \times (2:414 \times 10^{-5} \times 10^{247.8/(T-140)})$ Pas
Other parameter values, different parameters, additional parameters, and/or fewer parameters may be used.

The main difference between the Pennes and the Wulff-Klinger models lies in their cooling terms (i.e., the last term of the right-hand side). The former acts as a volumetric homogeneous heat sink whilst the latter accounts for the directional effect of blood flow on the tissue temperature field. Therefore, both equations can be easily implemented in a modular way to cope with tissue inhomogeneity, by using one or the other cooling term.

Large vessels are clearly identified in act 22, but small capillaries are difficult to image. Both types of vessels may be modeled by combining the Pennes and Wulff-Klinger models in a unified and modular framework. Assuming that blood vessels and the surrounding tissue are isolated from each other, the liver temperature $T_t$ is solved using the diffusion equation:

$$p_t c_t(\delta T_t/\delta t)=Q+del\cdot(d_t del\cdot T_t)$$

everywhere in the tetrahedral, mesh, or tissue sampling domain. The cooling term $H(Tb0-Tt)/(1-\epsilon)$ is added when a tetrahedron belongs to a large vessel (Pennes model) and $\epsilon p_b c_b v\cdot del\cdot T_t$ is added when the tetrahedron belongs to a small vessel or the parenchyma (Wulff-Klinger model). Other combinations may be used.

The biological heat transfer model may be responsive to one or more other models. One or more parameters of the biological heat transfer model are altered in one or more time increments based on the model of the ablation device, the heat sink model, and/or the tissue damage model.

For example, the heat source term Q varies according to the modeling of the ablation device in act 26. The biological heat transfer is modeled as a function of the heat source responsive to the modeling of the ablation device. Since the biological heat transfer model is a spatial model, the placement position of the modeled ablation device within the tissue region also alters the biological heat transfer. Placement variation may result in variation in the proximity and/or size of proximate vessels or other heat sinks.

As another example, the convective term or terms are responsive to the modeling of the heat sink. In the case of the liver, the hepatic blood vessels play a crucial role in determining the overall effectiveness of the radio frequency ablation procedure, since the hepatic blood vessels act as a heat sink and thus reduce the amount of heat that is delivered to the tissue. The heat sink activity of the blood vessels in the tissue causes the diffusion to be different at different locations. The blood flow in the vessels specific to the patient causes patient specific locations to limit changes in temperature due to carrying away the heat and bringing in mass with less heat. The convective terms respond to this heat sink operation.

In one embodiment, separate convection terms are provided for larger vessels for which a specific flow may be calculated, such as the feeder and tree vessels and for micro vessels which are not specifically identified from the imaging data. These terms are represented as flow and porous flow terms, respectively, with different convective terms. Additional, different, or fewer convective terms may be used. Other terms may alternatively or additionally be responsive to the heat sink model.

In that embodiment, the convective terms are present as volumetric anisotropic heat sink terms, $\beta^{perf}_{t,x}(T-T_b)$ and $\beta^{flow}_{t,x}(T-T_b)$, where the spatially-varying fields of parameters $\beta^{perf}_{t,x}$ and $\beta^{flow}_{t,x}$ are based on the blood density, specific heat, and perfusion or flow rate, while $T_b$ is the temperature of the blood. The blood temperature may be assumed or measured. The blood density and specific heat may be treated as constants or modeled to have variation with temperature. The heat sink term $\beta^{perf}_{t,x}(T-T_b)$ models perfusion based heat dissipation, due to micro-scale perfusion at the capillary level, and is approximately constant for homogenous tissue. This term approximates the convective term in the Wulff-Klinger model. On the other hand $\beta^{flow}_{t,x}(T-T_b)$ models macro-scale effects, and is related to the heat dissipation due to the blood flow within the larger vessels at the proximity of the tumor. This term is the cooling term of the modified Pennes model.

The heat sink model outputs the respective rates. The rates are used to establish the convection terms.

The adapting of the convection may be in addition to the selection of models based on vessel size used in the biological heat transfer model. The result is multiple sources of patient specific modeling. In other embodiments, these different adaptations for personalization are alternatives.

As another example, the bio heat transfer model responds to the output of the tissue damage modeling of act 28. As the simulation of the ablation device is modeled to increase temperature, cell necrosis occurs. This change in the tissue alters one or more of the diffusion characteristics. The survival fraction index, or other part of the tissue damage model indicates the change in a value of one or more parameters of the biological heat transfer model over time. For example, the Arrhenius equation is used to update the heat diffusion coefficient $\alpha_{x,t}$ and the thermal sinks $\beta^p_{x,t}$ and $\beta^f_{x,t}$ at every time step. This update is location dependent as different locations are subjected to different levels of heat. The input from the tissue damage modeling captures spatially inhomogeneous thermal property effect, and time dependent (e.g., temperature dependent) changes due to cell water evaporation, blood coagulation, and/or tissue necrosis.

The bio-heat transfer equations are solved using a finite element method (FEM). Test functions defined on linear tetrahedral elements, for instance, are used to discretize a weak form of the bio-heat equation (e.g., Garlekin's method). As a result, the heat diffusion is obtained by solving a linear system at every time step. Efficient implicit schemes may be used to have unconditional numerical stability, thus enabling large time steps for increased computational efficiency. A pre-requisite for FEM is the availability of detailed 3D tetrahedral, other meshes, or sampling of patient's liver. Once the anatomical model is generated, a virtual probe is placed and ablation is simulated using FEM.

In one example implementation of the finite element method on a tetrahedral mesh, the discretized equation: $M\dot{U}+KU=B$ is solved, with U the temperature, M the mass matrix, K the stiffness matrix for the diffusion, the reaction and the advection part, and B the vector including boundary conditions. Diffusion, reaction and advection terms are implemented in a modular way, but may be combined. The Neumann boundary conditions are used at the organ boundary. The heat source term is modeled through a Dirichlet boundary condition of 100° C. at the location of the virtual probe. The blood going through the liver is treated as a constant temperature of 37° C. For the advection term, a three-dimensional characteristic Galerkin scheme is used for numerical stability. First-order implicit Euler time discretization is employed. The resulting matrix system $Ax=B$ is solved using the conjugate gradient iterative algorithm. For the computational fluid dynamics, a full 3D Navier-Stokes viscous solver, expressed in an Eulerian framework which embeds the domain boundary using a level set representation of the segmented vessel is used. Other solutions or approaches for implementing the solution may be used.

Other numerical implementations may be used to solve the bio-heat equations. Finite differences or Lattice-Boltzmann methods on regular grids may be used. The liver boundary is represented using a level-set. This formulation is generalizable to moving boundaries and therefore directly applicable where the liver deformation under probe placement is simulated. Approximation of the bio-heat equation using an Eikonal equation (heat diffusion is seen as wave propagation) may be used. In this approximation, fast marching methods may yield computational optimization.

The computational approach for the simulation in act 24 of radio frequency ablation may be represented as: 1) estimate patient-specific model of liver anatomy, 2) compute 3D blood flow $\phi i$ and inlet pressures $p^-_i$ in hepatic vein, 3) compute portal vein upstream pressure p+ by fitting Darcy's model to the hepatic vein downstream pressures $p^-_i$ and flow $\phi i$, 4) compute 3D blood flow in portal vein, and 5) while $t<t_{end}$ do: 5 A) $t \leftarrow t+\Delta t$, 5B) update temperature T using Pennes model in the large vessels and Wulff-Klinger model elsewhere, and 5C) update cell-state. Other computational approaches may be used.

As an alternative to a computational approach, the simulation and/or one or more of the models are estimated using a machine-learnt detector or classifier. The machine-learnt classifier is trained before estimation of the model for a given patient, such as days, weeks, months, or years before. A set of training data from different patients is filtered or processed to obtain input features for the training or the training data itself is used as the input feature. A large pool of features may be extracted. The training determines the most determinative features for a given classification and discards lesser or non-determinative features. To prepare the set of training samples, ground truth temperature diffusion is provided, such as using magnetic resonance temperature mapping. Any number of expert annotated frames of data is used.

The detector is trained from the training data set using a computer. A data-driven, learning-based algorithm is applied to the training data. Using machine learning, the classifier is trained. The machine-trained classifier is any one or more classifiers. The classifier may be a model or detector using imaging processing, filtering, or other techniques. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used.

Once trained, a matrix is output. The matrix represents the learnt algorithm for simulation from preoperative data or features derived from the preoperative data. For application, the preoperative data or derived features, including probe placement and power, from a specific patient are input to the matrix. As an output, the matrix indicates the temperature distribution in space over time and/or output values for one of the models of the simulation (e.g., outputs blood velocity or other biological heat transfer parameter values). The output may also include probabilistic information, such as associated with alternative values. The machine-learnt detector estimates the parameters of the model from the preoperative data.

Figure 2:
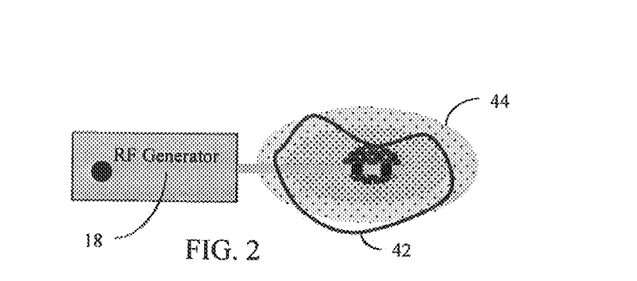
FIG. 2 is an illustration of an arrangement for ablation and a predicted heat diffusion.

The proposed framework has been evaluated on one patient-specific geometry extracted from pre-operative CT images. The virtual probe is placed in within the middle of the tumor as represented in FIG. 2. Cells within a sphere around the probe tip are heated at 100° C. to mimic the topology of the probe. The protocol to be clinically used is simulated as: heating for 10 minutes, stopping the heating for the next 5 minutes, and repeat the process by increasing the sphere diameter from 10 mm to 20 mm and finally 30 mm. Using just the Pennes Model, the model is able to predict the cooling effect of the big veins. The distribution of the temperature over the liver is returned, as represented by the contour 42 in FIG. 2. The dot pattern 44 shows temperature without the effects of heat sinks.

Referring again to FIG. 1, a map of temperature from the ablation device is computed in act 34. The temperature diffusion output by the biological heat transfer modeling provides the map. The map represents the temperature at different locations at a given time. FIG. 2 shows the temperature 44 mapped to four levels, the last level being background or normal. Any mapping range, resolution, or function may be used, such as a linear mapping with 5° C. increments. By mapping to ranges, iso-temperature contours are provided. The temperature map 44 of FIG. 2 is without modeling heat sinks. The contour 42 represents temperature with the modeling of the heat sinks.

A sequence of maps represents the temperature at different times. Alternatively, the temperature as a function of time for each location is used to derive a value, such as a maximum, average, or median, and the value is mapped to represent temperature as a function of location with the time axis collapsed.

In act 36, the diffusion of temperature is indicated. An image of the map of temperature is displayed or output. The image represents the tissue region of interest, such as the liver or part of the liver having a tumor. The image is formed at any resolution. Temperature may be interpolated to the display grid or greater resolution. Alternatively, the temperature is indicated by a value, graph, or chart.

Any type of image may be generated. For example, the image is three-dimensionally rendered from the temperature diffusion. Using a user or processor selected point of view with or without a lighting model, the temperature representing the volume is rendered to a two-dimensional display. Any volume rendering may be used, such as projection or surface rendering. In another example, a planar reconstruction is generated from the temperature. A user or processor placed slice plane or image plane is positioned relative to the volume. The temperatures representing or interpolated to represent the plane are used to generate the two-dimensional image. For multi-planar reconstruction, multiple planes are defined through the volume. An image is generated for each plane.

Figure 3:
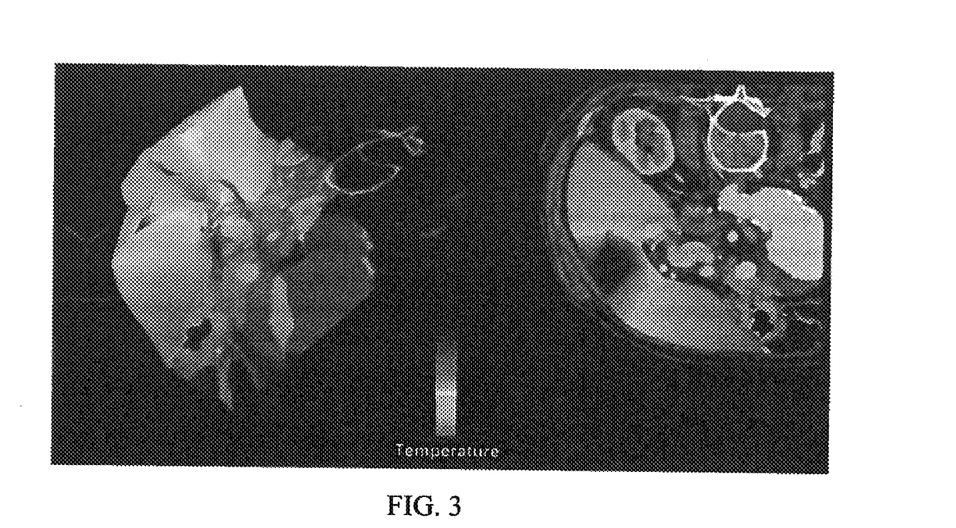
FIG. 3 is an example output image of heat diffusion.

The image or images of temperature are shown alone or without other non-temperature images. A sequence of such images may be shown, such as rendering from a sequence of volumes from different time increments. Alternatively, the image or images are shown with other information. The image may be separate but share the display screen with an image generated from the preoperative data. The temperature may be overlaid on the anatomy image, such as rendering the temperature with a different color, brightness or other characteristic. The rendered model is added to the CT image. FIG. 3 shows temperature mapped to CT cross-section images. The temperature overlay is a modulation, such as color modulation.

Iso-thermal contours, streamlines, other diffusion representations, or combinations thereof may be calculated and used to form one or more graphics. The graphics are overlaid with the anatomical and/or temperature map information. Alternatively, the graphics are displayed separately.

In one embodiment, the liver temperature is visualized using color maps and isothermal contours. The contours indicate regions that suffered similar heat. The evolution of the average temperature within a region of interest previously selected by the user may be displayed in an interactive way. The user may fine-tune the ablation parameters (probe location, probe orientation, and/or electrical or other power) interactively to pre-plan the ablation procedure. Optimal ablation of the region of interest may be planned. Streamlines may also be displayed to understand the effects of heat sinks in the ablation procedure. Necrotic areas are visualized using iso-contours of the survival fraction index. These post-processing functionalities are available in real-time to allow user interaction in planning.

Other features may be included in the image. For example, the modeled ablation device and/or an indication of the location being modeled is added to the image. As another example, an overlay or other indication of tissue necrosis is added as well as temperature. Other modeled values may be used for imaging.

In alternative or additional embodiments, the temperature is used for quantification. A change, maximum, average, or other quantity is calculated from the temperatures.

In act 38, the optimal, better, or sufficient probe location is determined. An optimal solution for probe location, power, application sequence, or other variance in ablation is automatically sought. Rather than rely on user feed back, the temperature diffusion and corresponding necrosis associated with different locations and/or other variance in ablation is compared to the region to be treated. For example, the position, power level, and sequence of application resulting in the greatest, sufficient, or complete coverage of the tumor and least necrosis of healthy tissue is found by simulating different combinations. By successively computing the thermal dose for a number of needle placements, the placement with maximum coverage on the tumor is found. In a successive optimization loop to solve for the probe location, orientation, and/or other characteristic, the combination for maximum tumor thermal dose coverage is found. The thermal dose coverage may be measured as the area defined by temperatures higher than a threshold (e.g., 70 degrees Celsius). Other measures may be used, such as a weighted measure that most strongly weights necrosis of the tumor while considering avoidance of necrosis outside the tumor.

The simulation may be integrated with on-going ablation or temperature measurements from a previous ablation. Temperature readings from thermistors or temperature MRI are used to validate the simulation. These actual temperatures may be used to further personalize the model parameters for patient-specific simulation results. The parameters used in the simulation are adapted to the actual temperatures using inverse problem algorithms. An optimization loop iteratively updates the model parameters (e.g., diffusion coefficients, convective terms, or others) such that the difference between simulation and observation is minimized. Kalman filtering, variational approaches, or other optimization methods that do not rely on derivatives may be used. Derivative-based optimization may be used in other embodiments.

In another embodiment, the simulation of ablation also simulates probe insertion prior to ablation. The insertion may move vessels relative to the tumor, cause flow differences, or result in spatial distortion in the region of interest. Biomechanical properties of the liver may be considered to predict the local deformations of the tissue due to the insertion of the probe. The local deformations are integrated into the vessel locations and/or mesh for solving the simulation. Ribs and other organs, segmented from preoperative data, may be considered to find the optimal path of the probe.

Figure 4:
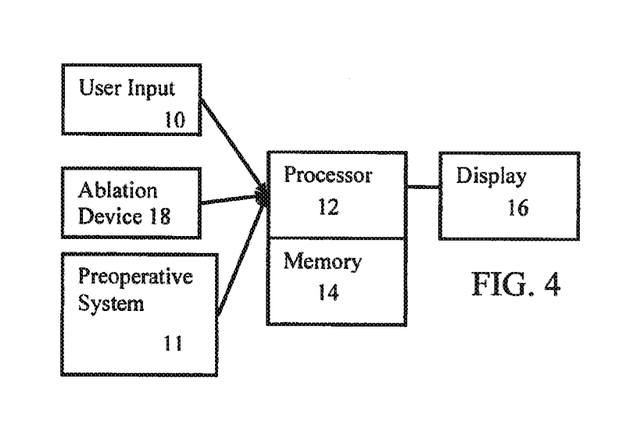
FIG. 4 is a block diagram of one embodiment of a system for patient specific computation of a temperature map under ablation therapy.

FIG. 4 shows a system for patient specific temperature mapping. The system includes an ablation device 18, an angiography or other preoperative system 11, a processor 12, a memory 14, a user input 10, and a display 16. The preoperative system 11 is shown as one system, but may be multiple systems, such as CT and MR. For example, MR or CT system is used for segmenting the organ or tissue and angiography is used for vessel segmentation. The processor 12, user input 10, display 16, and the memory 14 are shown separate, such associated with being a computer or workstation apart from the preoperative system 11. In other embodiments, the processor 12, user input 10, display 16, and/or memory 14 are part of the preoperative system 11. In alternative embodiments, the system is a workstation, computer, or server for simulating ablation using data acquired by a separate system or systems in real-time or using previously acquired patient-specific data stored in a memory. For example, the angiography system 11 is provided for acquiring patient data representing a volume, and a separate database, server, workstation, and/or computer is provided for simulating ablation. Additional, different, or fewer components may be used.

The computing components of the system, such as the preoperative system 11 and/or the processor 12 are configured by hardware, software, and/or design to perform calculations or other acts. The computing components operate independently or in conjunction with each other to perform any given act. The act is performed by one of the computer components, another of the computing components, or a combination of the computing components. Other components may be used by the computing components to scan or perform other functions.

For ablation guidance, the ablation device 18 is one to be used, such as a radio frequency ablation device. A probe, such as a catheter, with electrodes at a tip is used to ablate. The electrodes are used to create heat conducted into the surrounding tissue, causing coagulative necrosis at temperatures between 50° C. and 100° C. For ablation planning, the ablation device 18 is modeled, so an actual ablation device 18 may not be provided. The model is of a specific or class of ablation devices 18.

The user input 10 is a button, slider, knob, keyboard, mouse, trackball, touch screen, touch pad, combinations thereof, or other now known or later developed user input devices. The user may operate the user input 10 to interact with the system, such as the processor 12. For example, the user indicates an ablation device to be simulated, a probe position, location indication for segmenting, a dose sequence, a power or current, a viewing direction, rendering parameters, and/or simulation parameter values. The user input 10 receives the user input, which is passed to or used by the processor 12.

The preoperative system 11 is any now known or later developed angiography system. For example, a computed tomography system with a gantry, x-ray source, and detector is used to scan a patient. The patient has contrast agent to highlight the vessel structure. As a result, data representing vessels of the patient in a tissue region is output. The data may also represent other structures, such as the tissue. The angiography system 11 may output segmented data or output data for segmentation by the processor 12.

Alternatively or additionally, the preoperative system 11 is a CT, MR, x-ray, fluoroscopy, PET, SPECT, or ultrasound system. The preoperative system 11 is configured to acquire the preoperative data for simulation specific to a given patient. The data is acquired by scanning the patient and/or by receiving signals from the patient.

A frame or set of data representing a volume or plane is provided in response to the scanning. Each frame represents the scan region at a given time or over a period. Different frames are provided for different volumes and/or times. Different frames are provided for repetition of the scans for a same volume.

The memory 14 is a buffer, cache, RAM, removable media, hard drive, magnetic, optical, database, or other now known or later developed memory. The memory 14 is a single device or group of two or more devices. The memory 14 is within the preoperative system 11, part of a computer with the processor 12, or is outside or remote from other components.

The memory 14 stores the preoperative data, models, parameter values, images, segmented data, or other information. The memory 14 stores preoperative data representing a volume, segmented locations, and/or a mesh. The data represents a three-dimensional region. Any format may be used, such as voxels interpolated to a three-dimensional grid or data representing parallel or non-parallel planes.

The memory 14 is additionally or alternatively a non-transitory computer readable storage medium with processing instructions. The memory 14 stores data representing instructions executable by the programmed processor 12 for patient specific temperature mapping. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, three-dimensional data processor, graphics processing unit, application specific integrated circuit, field programmable gate array, digital circuit, analog circuit, combinations thereof, or other now known or later developed device for processing medical data. The processor 12 is a single device, a plurality of devices, or a network. For more than one device, parallel or sequential division of processing may be used. Different devices making up the processor 12 may perform different functions, such as a segmentor as one device and a separate device for simulating ablation. The processor 12 operates pursuant to stored instructions to perform various acts described herein.

The processor 12 is configured to predict ablation results in the tissue region of the patient from a model of the ablation device, a position of the modeled ablation device, a model of heat sink operation of the vessels, and a model of diffusion of heat due to the model of the ablation device, heat sink operation, and the position. Additional, different, or fewer models and/or parameters may be used for predicting ablation results, such as including a model of tissue damage. The models are implemented as equations, computational solutions, machine-learnt matrices, or other function.

The prediction performed by the processor 12 is automated. Alternatively, the prediction is based, in part, on a current or other power setting from the user input 10. The prediction may be based, in part, on a position and/or orientation input from the user input 10. Based on the inputs, the distribution of heat over time and space is simulated by the processor 12.

The processor 12 is configured to output an image of the predicted ablation results to the display 16. The image is a temperature map or temperature as a function of location. The image may alternatively or additionally include anatomy, iso-contours, streamlines, treatment region, tumor designation, predicted necrosis region, or other information. A sequence of images showing change over time or an image representing a given time (e.g., final results of simulated ablation) is displayed. In another embodiment, a value is output. The value represents temperature or is a measure of the completeness of coverage (e.g., a measure of estimated success of the planned treatment).

The display 16 is a CRT, LCD, plasma, projector, printer, or other output device for showing an image. The display 16 displays an image, which includes information from the prediction of ablation. A value of a measurement may be displayed. The value may be displayed in a chart, graph, and/or on an image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for patient specific computation of a temperature map under ablation therapy, the method comprising:

acquiring, with an imaging system, data representing vessels and tissue in a tissue region of a patient;

modeling a heat sink in the tissue with a computational fluid dynamics model, modeling of the heat sink being a function of locations of the vessels in the tissue region of the patient from geometrical data and blood flow boundary conditions acquired from the data representing the vessels and the tissue region, or nominal physiological values;

modeling biological heat transfer in the tissue region as a function of tissue thermal conductivity, modeling biological heat transfer in the tissue region as a function of small scale perfusion based on vasculature flow computed from computational fluid dynamics, calculating a temperature boundary condition from a model of an ablation device, and computing a temperature map comprising the boundary conditions, with the modeling of the heat sink, the modeling of the biological heat transfer as a function of the tissue thermal conductivity, and the modeling of the biological heat transfer as a function of the small scale perfusion.

2. The method of claim 1 wherein acquiring comprises segmenting locations in three-dimensions of the vessels and the tissue from imaging information of the imaging system.

3. The method of claim 1 wherein modeling the heat sink comprises computing flow rate in the vessels using computational fluid dynamics and patient-specific boundary conditions.

4. The method of claim 1 wherein modeling the heat sink comprises:
computing feed flow rate in feeding vessels along three-dimensional vessel paths; and
computing tree flow rate in tree vessels based on length and radius in one-dimension, the tree vessels smaller than the feeding vessels.

5. The method of claim 4 wherein modeling the biological heat transfer in the tissue region as a function of small scale perfusion comprises computing perfusion flow rate as a function of the feed and tree flow rates at the level of vasculatures, given the boundary conditions calculated by the computational fluid dynamics model.

6. The method of claim 1 wherein modeling the biological heat transfer comprises modeling as a partial differential equations where spatio-temporal variations of temperature are driven by a transient heat diffusion term, a heat source term, and a convective term, the convective term responsive to the modeling of the heat sink.

7. The method of claim 1 wherein modeling the biological heat transfer comprises modeling as a function of density of the tissue in the tissue region, specific thermal capacity constant of the tissue, and an anisotropic thermal conductivity matrix.

8. The method of claim 1 wherein modeling the biological heat transfer comprises modeling temperature variation as a function of flow convective and perfusion convective terms based on flow and perfusion rates, respectively, the flow and perfusion rates being obtained from the modeling of the heat sink.

9. The method of claim 1 wherein modeling the biological heat transfer comprises solving for a temperature distribution field as a function of space and time.

10. The method of claim 1 wherein generating the map comprises outputting temperature as a function of time and space from the modeling of the biological heat transfer.

11. The method of claim 1 further comprising displaying an image representing the tissue region with one or more of an overlay of color, isothermal contour, or streamline representing the temperature map.

12. The method of claim 1 wherein modeling the ablation device comprises modeling as a function of resistance, current, and time;
wherein modeling the biological heat transfer comprises modeling the biological heat transfer as a function of a heat source responsive to the modeling of the ablation device.

13. The method of claim 1 further comprising modeling tissue damage as a function of a survival fraction index and an Arrhenius equation;
wherein modeling the biological heat transfer comprises modeling the biological heat transfer as a function of heat effects on tissue represented as a function of the survival fraction index through an Arrhenius equation.

14. The method of claim 1 further comprising receiving user indication of a placement position of the ablation device;
wherein modeling the biological heat transfer comprises modeling spatially based on the placement position in the tissue region; and
further comprising displaying an image with a representation of the placement position.

15. The method of claim 1 further comprising solving for a probe location of the ablation device in the tissue region, the probe location being one of multiple possible probe locations and being the one of the possible probe locations corresponding to maximum thermal dose coverage.

16. A non-transitory computer readable storage medium having stored therein data representing instructions executable by a programmed processor for patient specific computation of a temperature map under ablation therapy, the storage medium comprising instructions for:
simulating heat generation by an ablation device modeled as a function of current, resistance, and time;
simulating diffusion over time of the heat in tissue in a tissue region of a patient, the diffusion responsive to heat sink operation of blood vessels in the tissue region of the patient, the blood vessels being specific to the patient, and the diffusion responsive to time-varying tissue response to the heat of the tissue, the diffusion simulation comprising calculating a rate of flow and a rate of perfusion for the blood vessels, modeling the time-varying tissue response as tissue damage from the ablation device, and modeling the diffusion as a biological heat transfer in the tissue; and
indicating the diffusion,
wherein the heat sink in the tissue is modeled with a computational fluid dynamics model, modeling of the heat sink being a function of locations of the vessels in the tissue region of the patient from geometrical data and blood flow boundary conditions acquired from data representing the vessels and the tissue region, or nominal physiological values.

17. The non-transitory computer readable storage medium of claim 16 wherein indicating the diffusion comprises outputting an image of heat iso-curves and a necrotic region, the heat iso-curves and the necrotic region being a function of the diffusion.

18. A system for patient specific computation of a temperature map under ablation therapy, the system comprising:
an ablation device;
an imaging system configured to scan a patient and output data representing a tissue region and vessels in the tissue region; and
a processor configured to predict ablation results in the tissue region of the patient from:
(1) a model of the ablation device as a function of current, resistance, and time,
(2) a position of the modeled ablation device,
(3) a model of heat sink operation of the vessels, wherein the model of the heat sink is a computational fluid dynamics model, the model of the heat sink being a function of locations of the vessels in the tissue region of the patient from geometrical data and blood flow boundary conditions acquired from the data representing the vessels and tissue region, or nominal physiological values, and (4) a model of diffusion of heat due to the model of the ablation device, the model of the heat sink operation, and the position of the modeled ablation device.

19. The system of claim 18 further comprising:

a user input, wherein the processor is configured to predict as a function of a current from the user input, and wherein the position of the modeled ablation device is a function of a placement from the user input;

a display, wherein the processor is configured to output an image of the predicted ablation results to the display.

* * * * *